(12) United States Patent
Aruffo et al.

(10) Patent No.: US 6,472,510 B1
(45) Date of Patent: Oct. 29, 2002

(54) CD40 RECEPTOR LIGANDS

(75) Inventors: Alejandro A. Aruffo, Edmonds; Jeffrey A. Ledbetter, Seattle, both of WA (US); Ivan Stamenkovic, Brookline, MA (US); Randolph Noelle, Plainfield, NH (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 08/338,975

(22) Filed: Nov. 14, 1994

Related U.S. Application Data

(63) Continuation of application No. 07/835,779, filed on Feb. 14, 1992, now abandoned.

(51) Int. Cl.$^7$ .................... C07K 14/705; C07K 14/71; C07K 16/46

(52) U.S. Cl. .................... 530/387.3; 530/350; 530/866

(58) Field of Search .................... 424/1.41, 1.49, 424/1.57, 130.1, 133.1, 139.1, 141.1, 143.1, 144.1, 153.1, 154.1, 173.1, 178.1, 181.1, 183.1, 184.1, 185.1, 192.1; 530/387.1, 387.9, 388.1, 388.12, 388.73, 388.75, 391.1, 391.3, 391.7, 350, 566, 868, 86 F; 514/2, 12; 435/69.1, 69.6, 69.7, 70.1, 70.21, 71.1, 326, 328, 331, 332, 334, 343.1, 343.2, 346, 252.3; 536/23.1, 23.4, 23.5, 23.53

(56) References Cited

U.S. PATENT DOCUMENTS

| 4,956,454 A | * | 9/1990 | Heffernan et al. |
| 5,247,069 A | * | 9/1993 | Ledbetter .................... 530/350 |
| 5,434,131 A | * | 7/1995 | Linsley |
| 5,474,771 A | | 12/1995 | Lederman et al. |
| 5,683,693 A | | 11/1997 | Noelle et al. |
| 5,962,406 A | * | 10/1999 | Armitage et al. |

FOREIGN PATENT DOCUMENTS

| WO | WO 93/08207 | 4/1993 |
| WO | WO 93/09812 | 5/1993 |
| WO | WO 97/20063 | 6/1997 |

OTHER PUBLICATIONS

I. Harris Et Al. TBTECH 11:42–44(1993).*
L. Steiwer Et Al Biotechnology 11: 644(1993).*
Marshall Et Al. J Clin Immunol. 13 :165–174(1993).*
Armitage et al., 1992, Nature 357:80.
Lederman et al., 1992, J. Exp. Med. 175:1091–1101.
Noelle et al., 1992, Proc. Natl. Acad. Sci. U.S.A. 89:6550–6554.
Yellin et al., 1991, J. Immunol. 147:3389–3395.
Hollenbaugh Et Al. EMBO J. 11: 4313–4321(1992).
Aruffo Et Al. Cell 72: 291–300(1993).
Stamenkovic Et Al. EMBO Journal 8:1403–1410(1989).*
Noelle Et Al. JMMUNOL. Today 13 : 431–433(1992).*
Aruffo Et Al. Cell 61 : 1303–1313 (1990).*
Hodgkin Et Al. J. Immunol. 145 : 2025–2034 (1990).*
Bartlett Et Al. J. Immunol. 145: 3956–3962 (1990).*
Paulie Et Al. J. Immunol. 142: 590–595 (1989).*
Dillmon Annals Int. MAED 111:592–603 (1989).*
Waldmann Science 252: 1657–1662(1991).*
Hollenbaugh Et Al. Curr. Opin. Immunol. 4:216–219 (1992).*
Clark, Edward A., 1990, "CD40: A cytokine receptor in search of a ligand," *Tissue Antigens* 35:33–36.
Noelle et al., 1992, "CD40 and its ligand, an essential ligand–receptor pair for thymus–dependent B–cell activation," *Immunology Today* 13(11):431–433.
Lane et al., 1992, "Activated human T cells express a ligand for the human B cell–associated antigen CD40 which participates in T cell–dependent activation of B lymphocytes," *Eur. J. Immunol.* 22:2573–2578.
Graf et al., 1992, "Cloning of TRAP, a ligand for CD40 on human T cells," *Eur. J. Biochem.* 22:3191–3194.
Hollenbaugh et al., Journal of Immunol. Methods, vol. 188, pp. 1–7 (1995).
Durie et al., Science, vol. 261, pp. 1328–1330 (1993).
Foy et al., J. Exp. Med., vol. 178, pp. 1567–1575 (1993).
Nonoyama et al., J. Exp. Med., vol. 178, pp. 1097–1102 (1993).
Marshall et al., Journal of Immunol., vol. 152(10), pp. 4816–4825 (1994).
Ochs et al., Immunology, vol. 6, pp. 337–341 (1994).
Current Protocols in Immunology, Supplement 4, Unit 10.19–1 to 1019–10.
Noelle et al., Immunology Today, vol. 13, No. 11, pp. 431–433 (1992).
Clark et al., Tissue Antigens, vol. 35, pp. 33–36 (1990).
Armitage et al., Nature, vol. 357, pp. 80–82 (1992).
Lane et al., Eur. J. Immunol., vol. 22, pp. 2573–2578.
Noelle et al., Proc. Natl. Acad. Sci., vol. 89, pp. 6550–6554 (1992).
Graf et al., Eur. J. Immunol., vol. 22, pp. 3191–3194 (1992).
Bartlett et al., The Journal of Immunology, vol. 145, No. 12, pp. 3956–3962 (1990).

(List continued on next page.)

Primary Examiner—Phillip Gambel
(74) Attorney, Agent, or Firm—Joan E. Switzer

(57) ABSTRACT

The present invention relates to a counter-receptor, termed CD40CR, for the CD40 B-cell antigen, and to soluble ligands for this receptor, including fusion molecules comprising at least a portion of CD40 protein. It is based, at least in part, on the discovery that a soluble CD40/immunoglobulin fusion protein was able to inhibit helper T-cell mediated B-cell activation by binding to a novel 39 kD protein receptor on helper T-cell membranes. The present invention provides for a substantially purified CD40CR receptor; for soluble ligands of CD40CR, including antibodies as well as fusion molecules comprising at least a portion of CD40 protein; and for methods of controlling B-cell activation which may be especially useful in the treatment of allergy or autoimmune disease.

8 Claims, 10 Drawing Sheets

OTHER PUBLICATIONS

Figure 1A:
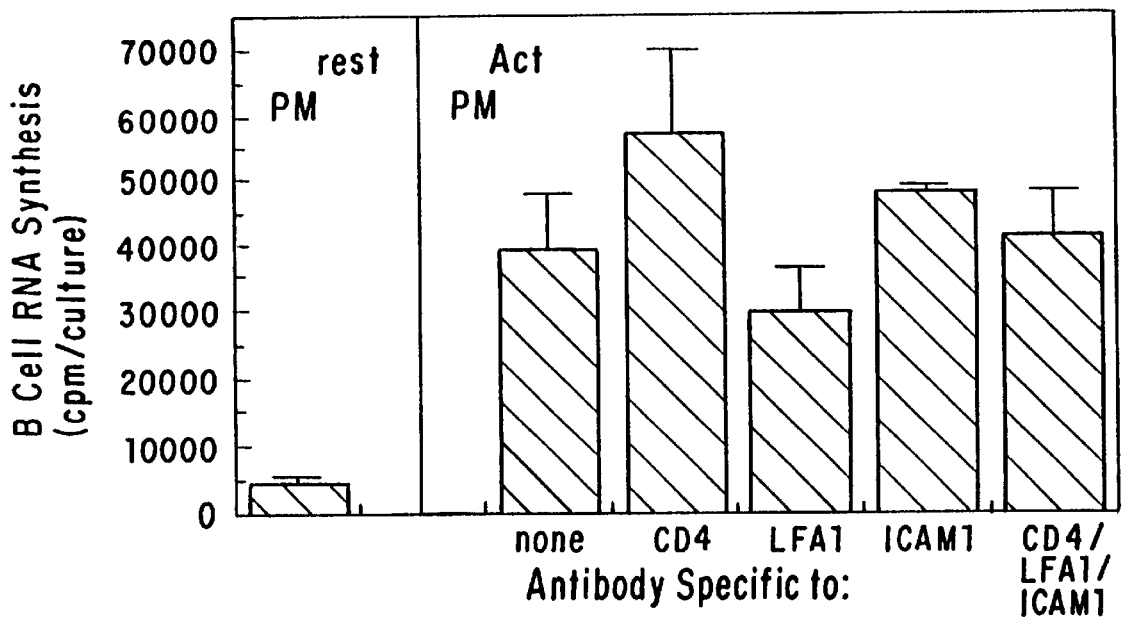

Behar et al., J. Exp. Med., vol. 182, pp. 2007–2018 (1995).
Biancone et al., Kidney International, vol. 48, pp. 458–468 (1995).
Borrebaeck et al., Immunology Today, vol. 14, No. 10, pp. 477–479 (1993).
Clark et al., Annu. Rev. Immunol., vol. 127, pp. 97–127 (1991).
Clark et al., Immunology, vol. 83, pp. 4494–4498 (1986).
Dillman, Annals of Internal Medicine, vol. 111, pp. 592–603 (1989).
Dorken et al., Leucocyte Typing IV (1989).
Harris et al., TIB TECH, vol. 11, pp. 42–44 (1993).
Gray et al., J. Exp. Med., vol. 180, pp. 141–145 (1994).
Hodgkin et al., The Journal of Immunology, vol. 145, pp. 2025–2034 (1990).
Konrad et al., Biological Barriers to Protein Delivery, vol. 4, pp. 409–437 (1993).
Larsen et al., Transplantation, vol. 61, No. 1, pp. 4–9 (1996).
Lederman et al., J. Exp. Med., vol. 175, pp. 1091–1101 (1992).
Marshall et al., Journal of Clinical Immunology, vol. 13, No. 3, pp. 165–174 (1993).
Paulie et al., The Journal of Immunology, vol. 142, No. 2, pp. 590–595 (1988).
Pfeffer et al., Cell, vol. 73, pp. 457–467 (1993).
Stamenkovic et al., The EMBO Journal, vol. 8, No. 5, pp. 1403–1410 (1989).
Stuber et al., J. Exp. Med., vol. 183, pp. 693–698 (1996).
Van den Eertwegh et al., J. Exp. Med., vol. 178, pp. 1555–1565 (1993).
Waldmann, Thomas A., Science, vol. 252, pp. 1657–1662 (1991).
Yellin et al., Journal of Immunology, vol. 147(10), pp. 3389–3395 (1991).
Hollenbaugh Et Al. Cell 72: 291–300(1993).*
Aruffo Et. Al. Cell 72: 291–300(1993).*

* cited by examiner

| Staining Ab or Fusion Protein | Blocking Ab | Resting $T_h$ | Activated $T_h$ |
|---|---|---|---|
| CD40 (50 μg/ml) | --- | 4.9 | 56.5 |
| MR1 (50 μg/ml) | --- | 5.7 | 61.8 |
|  |  |  |  |
| CD40 (50 μg/ml) | MR1 (50 μg/ml) | 5.0 | 11.7 |
| CD40 " " | MR1 (25 μg/ml) | --- | 20.7 |
| CD40 " " | MR1 (10 μg/ml) | --- | 30.3 |
| CD40 " " | MR1 ( 5 μg/ml) | --- | 49.5 |
| CD40 " " | α-α,β (50 μg/ml) | --- | 63.0 |

```
  1 GCCTCGCTCGGGCGCCCCAGTGGTCCTGCGCGCTGGTCTCACCTCGGCACTGGTTCTGCCCTCCCTGCAGTGCGTCCTCTGGGGCTGCTTGCTGACCGCTGTCCATCCAGAACCACCACTG
                                             M  V  R  L  P  L  Q  C  V  L  W  G  C  L  L  T  A  V  H  P  E  P  P  T  A
121 CATGCAGAGAAAAACAGTACCTAATAAACAGTCAGTCTGCTGTCTTCTTTGTCCAGCAGACAGAAACTGGTGAGTGACTGCACAGAGTTCACTGAAACGGAATGCCTTCCTTGCGGTGAAA
 26  C  R  E  K  Q  Y  L  I  N  S  Q  C  C  S  L  C  Q  P  G  Q  K  L  V  S  D  C  T  E  F  T  E  T  E  C  L  P  C  G  E  S
241 GCCGAATTCCTAGACACCTGGAACAGAGAGACACACTGCCACCAGCACAAATACTGCGACCCCAACCTAGGGCTTCGGGTCCAGCAGAAGGGCCACCTCAGAAACAGACACCATCTGCACCT
 66  A  E  F  L  D  T  W  N  R  E  T  H  C  H  Q  H  K  Y  C  D  P  N  L  G  L  R  V  Q  Q  K  G  T  S  E  T  D  T  I  C  T
361 GTGAAGAAGGCTGCACTGTACGAGTGAGGCCTGTGTCCTGCACCGCTGTGTCCTGCAAAATGTCACCCTTGGACACCTGTGAGACCAAGACCTGTGTCAACAGGCAGCACAAACAGACTGATGTTG
106  E  E  G  W  H  C  T  S  E  A  C  E  S  C  V  L  H  R  S  C  S  P  G  F  G  V  K  Q  I  A  T  G  V  S  D  T  I  C  E  P
                                                                                                                  --CHO--
481 CCTGCCCAGTCGGCTTCTTCTCCAATGTGTCATCTGCTTTCCAAAAATGTCACCCTTGGACACCTGTGAGACCAAGACCTGTGTCAACAGGCAGCACAAACAGACTGATGTTG
146  C  P  V  G  F  F  S  N  V  S  S  A  F  E  K  C  H  P  W  T  S  C  E  T  K  D  L  V  V  Q  Q  A  G  T  N  K  T  D  V  V
                  --CHO--                                                                                        --CHO--
601 TCTGTGGTCCCCAGGATCGGCTGAGAGCCCTGGTGGTGATCCCCATCATCTTCGGGATCCTCTTCGCCATCCTCTTGCTCGTTTGCCATCCTCGTGGCTGTGCTTTATCAAAAAGGTGGCCAAGAAGCCAACCAATA
186  C  G  P  Q  D  R  L  R  A  L  V  V  I  P  I  I  F  G  I  L  F  A  I  L  L  V  L  V  F  I  K  K  V  A  K  K  P  T  N  K
                             =  =  =  =  =  =  =  =  =  =  =  =  =  =  =  =  =  =  =  =  =  =
721 AGCCCCCCACCCCAAGCAGGAGAACCCCAGGAGTCAATTTCCCAGACATCTCCTGGCTCCAACACTGCTCCAGTGCAGGAGACTTTACATGGATGCCAACCGTCACCCAGGAGG
226  A  P  H  P  K  Q  E  P  Q  E  I  N  F  P  D  D  L  P  G  S  N  T  A  A  P  V  Q  E  T  L  H  G  C  Q  P  V  T  Q  E  D
841 ATGGCAAAGAGAGTCCATCTCAGTGCAGGAGACAGTGAGGCTGCCACGTGGCCAAACAGGCAGTTGGGCCACGAGGACCGCCACCAGGAGCCTGTGCTGCTGCAGGGGT
266  G  K  E  S  R  R  I  S  V  Q  E  R  Q
901 GCAGGCAGAAGCGGGAGCTATGCCCAGTCAGTGCCAGCCCCTC
```

FIG.8A

SEQUENCE LISTING

<160> NUMBER OF SEQ ID NOS: 3

<210> SEQ ID NO 1
<211> LENGTH: 1004
<212> TYPE: DNA
<213> ORGANISM: Homo sapiens

<400> SEQUENCE: 1

```
gcctcgctcg ggcgcccagt ggtcctgccg cctggtctca cctcgccatg gttcgtctgc      60
ctctgcagtg cgtcctctgg ggctgcttgc tgaccgctgt ccatccagaa ccacccactg     120
catgcagaga aaaacagtac ctaataaaca gtcagtgctg ttctttgtgc cagccaggac     180
agaaactggt gagtgactgc acagagttca ctgaaacgga atgccttcct tgcggtgaaa     240
gcgaattcct agacacctgg aacagagaga cacactgcca ccagcacaaa tactgcgacc     300
ccaacctagg gcttcgggtc cagcagaagg gcacctcaga aacagacacc atctgcacct     360
gtgaagaagg ctggcactgt acgagtgagg cctgtgagag ctgtgtcctg caccgctcat     420
gctcgcccgg ctttggggtc aagcagattg ctacaggggt ttctgatacc atctgcgagc     480
cctgcccagt cggcttcttc tccaatgtgt catctgcttt cgaaaaatgt caccttgga      540 caagctgtga gaccaaagac ctggttgtgc aacaggcagg cacaaacaag actgatgttg     600
tctgtggtcc ccaggatcgg ctgagagccc tggtggtgat ccccatcatc ttcgggatcc     660
tgtttgccat cctcttggtg ctggtcttta tcaaaaaggt ggccaagaag ccaaccaata     720
aggcccccca ccccaagcag gaacccagg agatcaattt tcccgacgat cttcctggct      780
ccaacactgc tgctccagtg caggagactt tacatggatg ccaaccggtc acccaggagg     840
atggcaaaga gagtcgcatc tcagtgcagg agagacagtg aggctgcacc cacccaggag     900
tgtggccacg tgggcaaaca ggcagttggc cagagagcct ggtgctgctg ctgcaggggt     960
gcaggcagaa gcggggagct atgcccagtc agtgccagcc cctc                     1004
```

```
<210> SEQ ID NO 2
<211> LENGTH: 277
<212> TYPE: PRT
<213> ORGANISM: Homo sapiens

<400> SEQUENCE: 2

Met Val Arg Leu Pro Leu Gln Cys Val Leu Trp Gly Cys Leu Leu Thr
 1               5                  10                  15

Ala Val His Pro Glu Pro Thr Ala Cys Arg Glu Lys Gln Tyr Leu
             20                  25                  30

Ile Asn Ser Gln Cys Cys Ser Leu Cys Gln Pro Gly Gln Lys Leu Val
             35                  40                  45

Ser Asp Cys Thr Glu Phe Thr Glu Thr Glu Cys Leu Pro Cys Gly Glu
     50                  55                  60

Ser Glu Phe Leu Asp Thr Trp Asn Arg Glu Thr His Cys His Gln His
 65                  70                  75                  80

Lys Tyr Cys Asp Pro Asn Leu Gly Leu Arg Val Gln Gln Lys Gly Thr
                 85                  90                  95

Ser Glu Thr Asp Thr Ile Cys Thr Cys Glu Glu Gly Trp His Cys Thr
                100                 105                 110

Ser Glu Ala Cys Glu Ser Cys Val Leu His Arg Ser Cys Ser Pro Gly
                115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
                180                 185                 190

Arg Ala Leu Val Val Ile Pro Ile Ile Phe Gly Ile Leu Phe Ala Ile
            195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
                260                 265                 270

Val Gln Glu Arg Gln
        275

<210> SEQ ID NO 3
<211> LENGTH: 6
<212> TYPE: PRT
<213> ORGANISM: Homo sapiens

<400> SEQUENCE: 3

Gly Pro Gln Asp Pro Glu
 1               5
```

CD40 RECEPTOR LIGANDS

This is a continuation of U.S. patent application Ser. No. 07/835,799, filed Feb. 14, 1992 (abandoned) which is incorporated by reference herein in its entirety.

This invention was made, in part, with government support under R01 AI26296 awarded by the National Institutes of Heath. The government has certain rights in the invention.

1. INTRODUCTION

The present invention relates to a counter-receptor, (also known as CD40 ligand), for the CD40 B-cell antigen, and to soluble ligands for this receptor, including fusion molecules comprising at least a portion of CD40 protein. It is based, at least in part, on the discovery that a soluble CD40/immunoglobulin fusion protein was able to inhibit helper T-cell mediated B-cell activation by binding to a novel 39 kD protein receptor on helper T-cell membranes. The present invention provides for a substantially purified CD40CR receptor; for soluble ligands of CD40CR, including antibodies as well as fusion molecules comprising at least a portion of CD40 protein; and for methods of, controlling B-cell activation which may be especially useful in the treatment of allergy or autoimmune disease.

2. BACKGROUND OF THE INVENTION

Studies by Mitchison, Benacerraf and Raff first suggested that physical interactions between $T_h$ and B-cells were essential in the development of humoral immune responses. Later studies documented that $T_h$ formed physical conjugates with class II major histocompatibility complex (MHC) compatible, antigen-presenting B-cells (Vitetta et al., (1987) Immunol. Rev. 99:193–239) and that it was the B-cells within these conjugates that responded to $T_h$ (Bartlett et al., (1989) J. Immunol. 143:1745–1754). With the discovery that $T_h$-derived lymphokines exerted potent growth and differentiative effects on B-cells, it was proposed that soluble factor(s) released in proximity by activated $T_h$ mediated the activation of the interacting B-cell. However, none of the molecularly cloned lymphokines, alone or in combination, manifested the ability to induce B-cell cycle entry. Unlike soluble factors, plasma membrane fractions from activated $T_h$ induced B-cell cycle entry (Hodgkin et al., (1990) J. Immunol. 145:2025–2034; Noelle et al., (1991) J. Immunol. 146:1118–1124). Studies using purified plasma membrane fractions from activated $T_h$ suggested that a protein expressed on the membrane of activated $T_h$ was responsible for initiating humoral immunity (Noelle et al., (1991) J. Immunol. 146:1118–1124; Bartlett et al., (1990) J. Immunol. 145:3956–3962).

Purified plasma membranes from activated $T_h$ ($PM^{Act}$) have been used to investigate the nature of this effector. function (Hodgkin et al. (1990) J. Immunol. 145:2025–2034; Noelle et al., (1991) J. Immunol. 146:1118–1124). $PM^{Act}$ from activated $T_h$, but not resting $T_h$ ($PM^{rest}$) expressed an activity that induced B-cell cycle entry in an antigen-nonspecific, class II-unrestricted manner. In addition, it was shown that the activity expressed by $PM^{Act}$ required 4–6 hours of activation, de novo RNA synthesis and was protein in nature (Bartlett et al., (1990) J. Immunol. 145:3956–3962).

3. SUMMARY OF THE INVENTION

The present invention relates to a counter-receptor, termed CD40CR, for the CD40 B-cell antigen, and to soluble ligands for this receptor, including fusion molecules comprising at least a portion of CD40 protein. It is based, at least in part, on the discovery that a soluble CD40/immunoglobulin fusion protein was able to inhibit helper T-cell mediated B-cell activation by binding to a novel 39 kD receptor protein (termed "CD40CR" for CD40 counter-receptor) on helper T-cell membranes, and on the discovery that a monoclonal antibody, termed MR1, directed toward this 39 kD receptor was able to inhibit helper T-cell mediated activation of B-cells.

The present invention provides for a substantially purified CD40CR receptor; for soluble ligands of CD40CR, including antibodies as well as fusion molecules comprising at least a portion of CD40 protein; and for methods of controlling B-cell activation.

In particular embodiments of the invention, B-cell activation in a subject may be inhibited by contacting helper T cells of the subject with effective amounts of a soluble ligand of CD40CR. Such inhibition of B-cell activation may be especially useful in the treatment of allergy or autoimmune disease.

One advantage of the present invention is that it enables intervention in an aspect of the immune response which is not antigen specific. Many current therapies for allergy include desensitization to particular antigens, and require that each patient be tested in order to identify antigens associated with sensitivity. Asia practical matter, exhaustive analysis of a patient's response to each and every potential allergen is virtually impossible. Furthermore, in most autoimmune conditions, the causative antigen is, generally, unknown or even irrelevant to the disease process. The present invention, which relates to the antigen nonspecific CD40/CD40CR interaction, circumvents the need to characterize the antigen associated with allergy or autoimmunity. Therefore, the present invention may be used to particular advantage in the treatment of allergic conditions in which the immunogen is not known, or has multiple components, for example, in hay fever or in procainamide induced lupus. It may also be useful in acute treatment of immune activation, for example, in therapy for anaphylaxis.

3.1. ABBREVIATIONS

| | |
|---|---|
| Ig | immunoglobulin |
| mab | monoclonal antibody |
| $PM^{Act}$ | plasma membranes prepared from activated helper T-cells |
| $PM^{rest}$ | plasma membranes prepared from resting helper T-cells |
| PAGE | polyacrylamide gel electrophoresis |
| rIL4 | recombinant interleukin 4 |
| rIL5 | recombinant interleukin 5 |
| SN | supernatant |
| $T_h$ | helper T-cell |
| $T_h1$ | refers to D 1.6, a I-$A^d$-restricted, rabbit immunoglubulin specific clone |

4. DESCRIPTION OF THE FIGURES

Figure 1B:
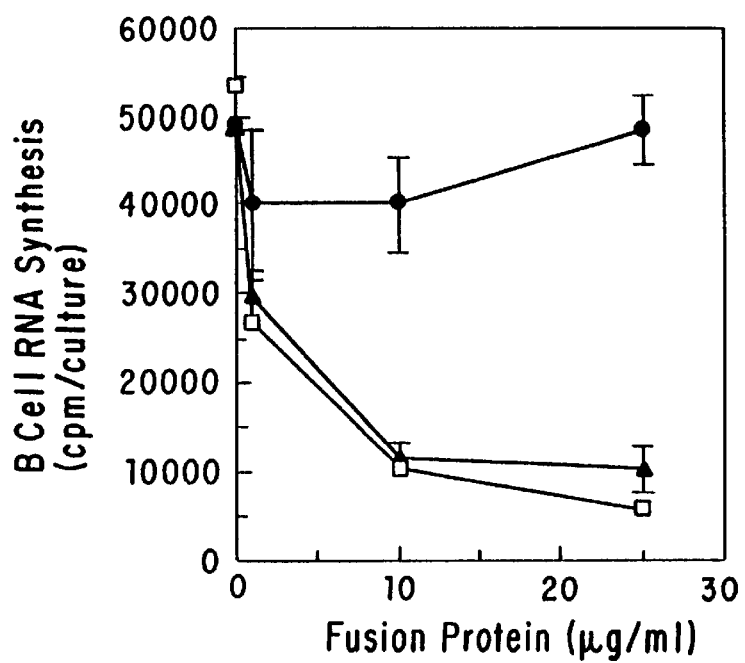
Figure 1C:
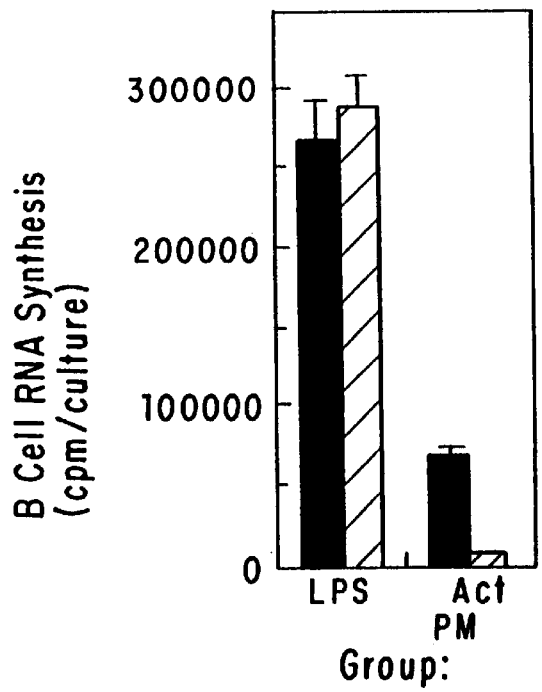

FIGS. 1A–1C. Effect of monoclonal antibodies and CD40-Ig on the induction of B-cell RNA synthesis by $PM^{Act}$.

FIG. 1A. Resting B-cells were cultured with $PM^{rest}$ or $PM^{Act}$ from $T_h1$. 25 µg/ml of anti-CD4, anti-LFA-1 or anti-ICAM-1 or a combination of each of these (each at 25 µg/ml) was added to wells containing $PM^{Act}$ and B-cell RNA synthesis was measured by incorporation of [$^3$H]-uridine.

B-cell RNA synthesis was assessed from 42 to 48 hours post-culture. Results presented are the arithmetic means of triplicate cultures+/−s.d., and are representative of 5 such experiments.

FIG. 1B. Resting B-cells were cultured with PM$^{Act}$ from T$_h$1 (●, ▲) or T$_h$2 (□). To the T$_h$1 PM$^{Act}$ containing cultures (●, ▲), increasing amounts of CD40-Ig (▲) or control protein CD7E-Ig(●) were added. To the T$_h$2 PM$^{Act}$ containing culture (□), increasing amounts of CD40-Ig were added. B-cell RNA synthesis was assessed from 42 to 48 hours post-culture. Results presented are the arithmetic means of triplicate cultures+/−s.d., and are representative of 3 such experiments.

FIG. 1C. Resting B-cells were cultured with LPS (50 μg/ml) or PM$^{Act}$. To cultures, CD40-Ig (25 μg/ml; hatched) or CD7E-Ig (25 μg/ml; solid) were added. RNA synthesis was determined as described in FIG. 1A. Results presented are the arithmetic mean of triplicate cultures+/−s.d., and are representative of 3 such experiments.

Figure 2A:
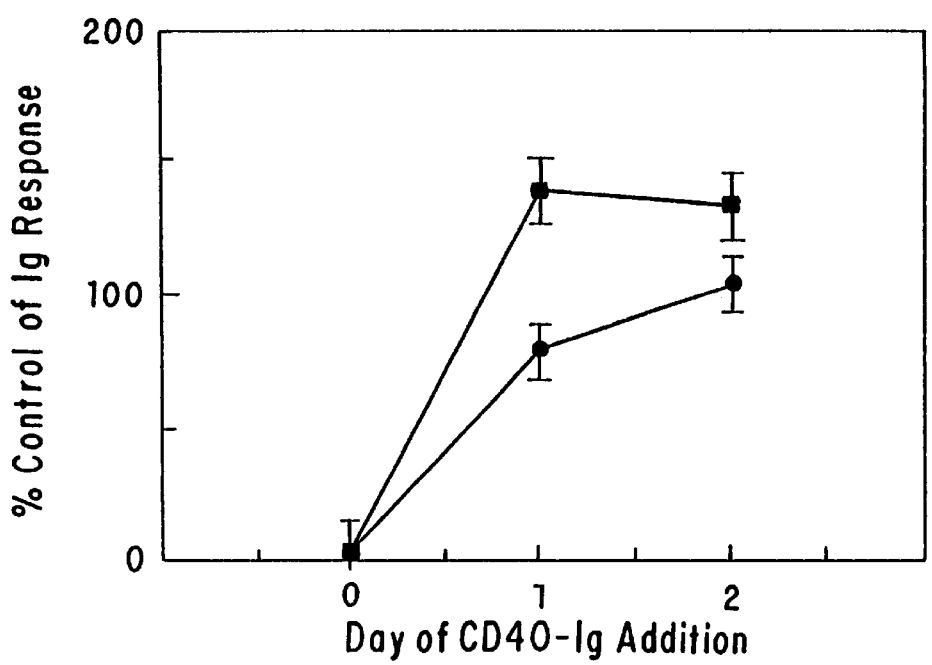
Figure 2B:
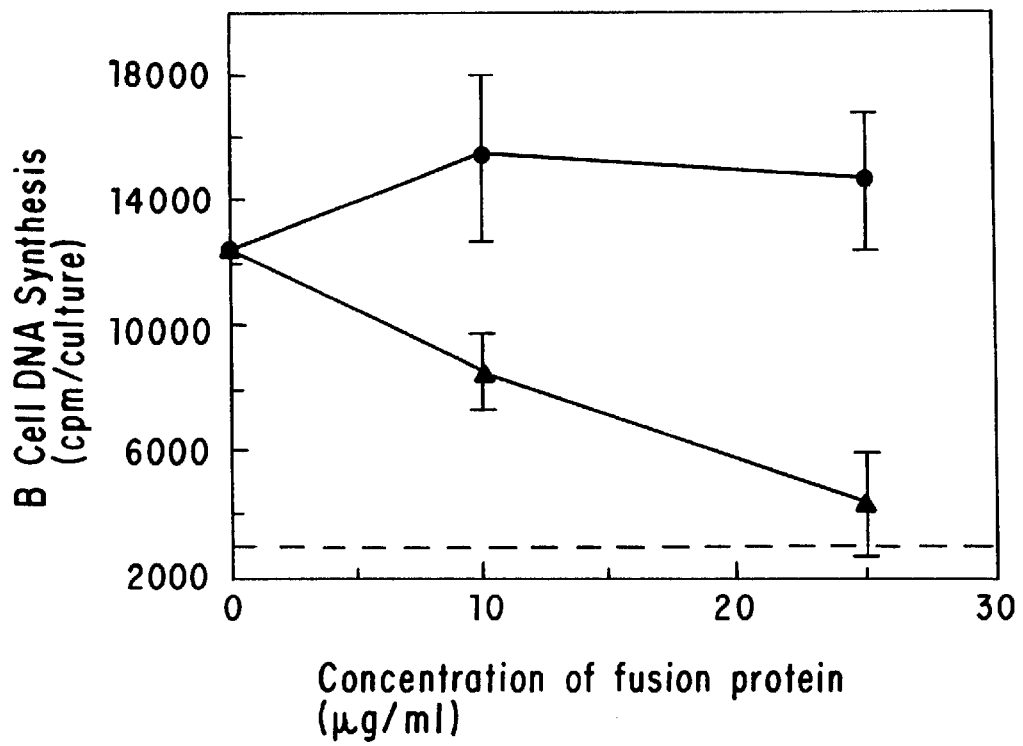

FIGS. 2A–2B. CD40-Ig inhibited B-cell differentiation and proliferation.

FIG. 2A. Resting B-cells were cultured with PM$^{Act}$, rIL4 (10 ng/ml) and rIL5 (5 ng/ml). Either at the initiation of culture, or on days 1, 2 or 3 post-initiation of culture, CD40-Ig or CD7E-Ig (25 μg/ml) were added. On day six of culture, SN from individual wells were harvested and quantitated for IgM(■) and IgG$_1$(●) using an anti-isotype specific ELISA, as described in (Noelle et al., (1991) *J. Immunol.* 146:1118–1124). In the presence of PM$^{Act}$, IL4 and IL5, (in the absence of added CD40-Ig) the concentrations of IgM and IgG$_1$ were 4.6 μg/ml and 126 ng/ml, respectively. Cultures which received CD7E-Ig (25 μg/ml) on Day 0 produced 2.4 μg/ml and 89 ng/ml of IgM and IgG$_1$, respectively. In the absence of IL4 and IL5, no IgM or IgG$_1$ was detected. Results are representative of 3 such experiments.

FIG. 2B. T$_h$1 were rested or activated with anti-CD3 for 16 hours, irradiated and cultured (1×10$^4$/well) with resting B-cells (4×10$^4$/culture) in the presence of IL4 (10 ng/ml). Between 0 and 25 μg/ml of CD40-Ig (▲) or CD7E-Ig (●) were added to cultures. From 66–72 hours post-culture, wells were pulsed with 1.0 μCi of [$^3$H]-thymidine and harvested. The dotted line indicates the response of B-cells to resting T$_h$. Results presented are the arithmetic mean of triplicate cultures+/−s.d., and are representative of 2 such experiments.

Figure 3A:
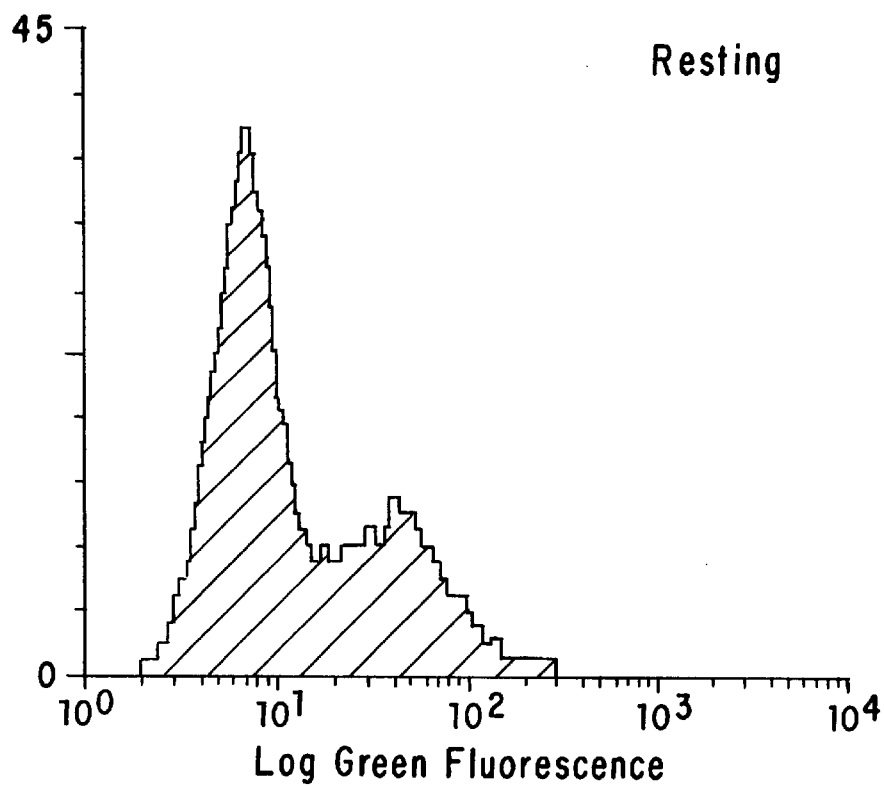
Figure 3B:
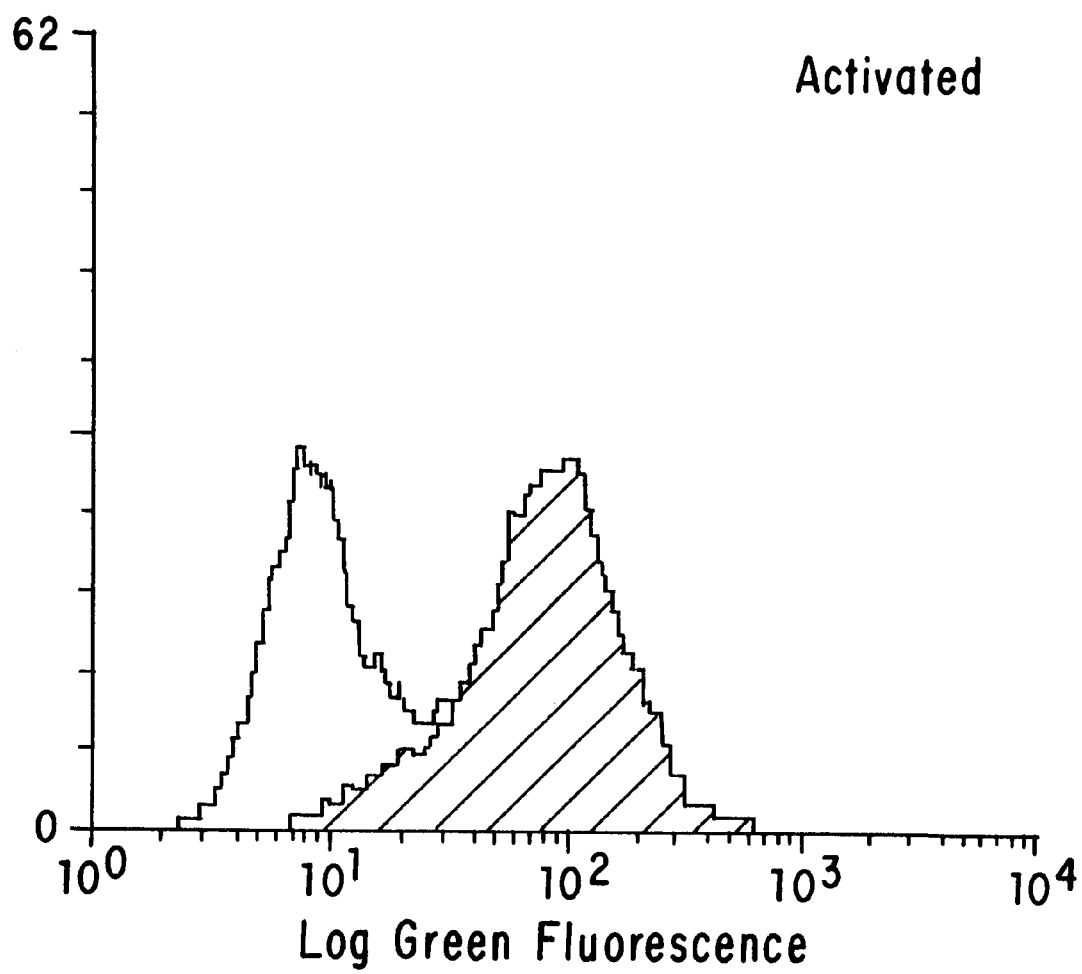

FIGS. 3A–3B. CD40-Ig detected a molecule expressed on activated, but not resting T$_h$. Resting (FIG. 3A) and activated (FIG. 3B) T$_h$ were harvested and incubated with fusion proteins for 20 minutes at 4° C., followed by FITC-conjugated goat anti-hIgG (25 μg/ml). Percentage positive cells and MFI were determined by analysis of at least 5000 cells/sample. Results are representative of 6 such experiments. CD40-Ig binding is indicated by a filled-in profile.

Figure 4:
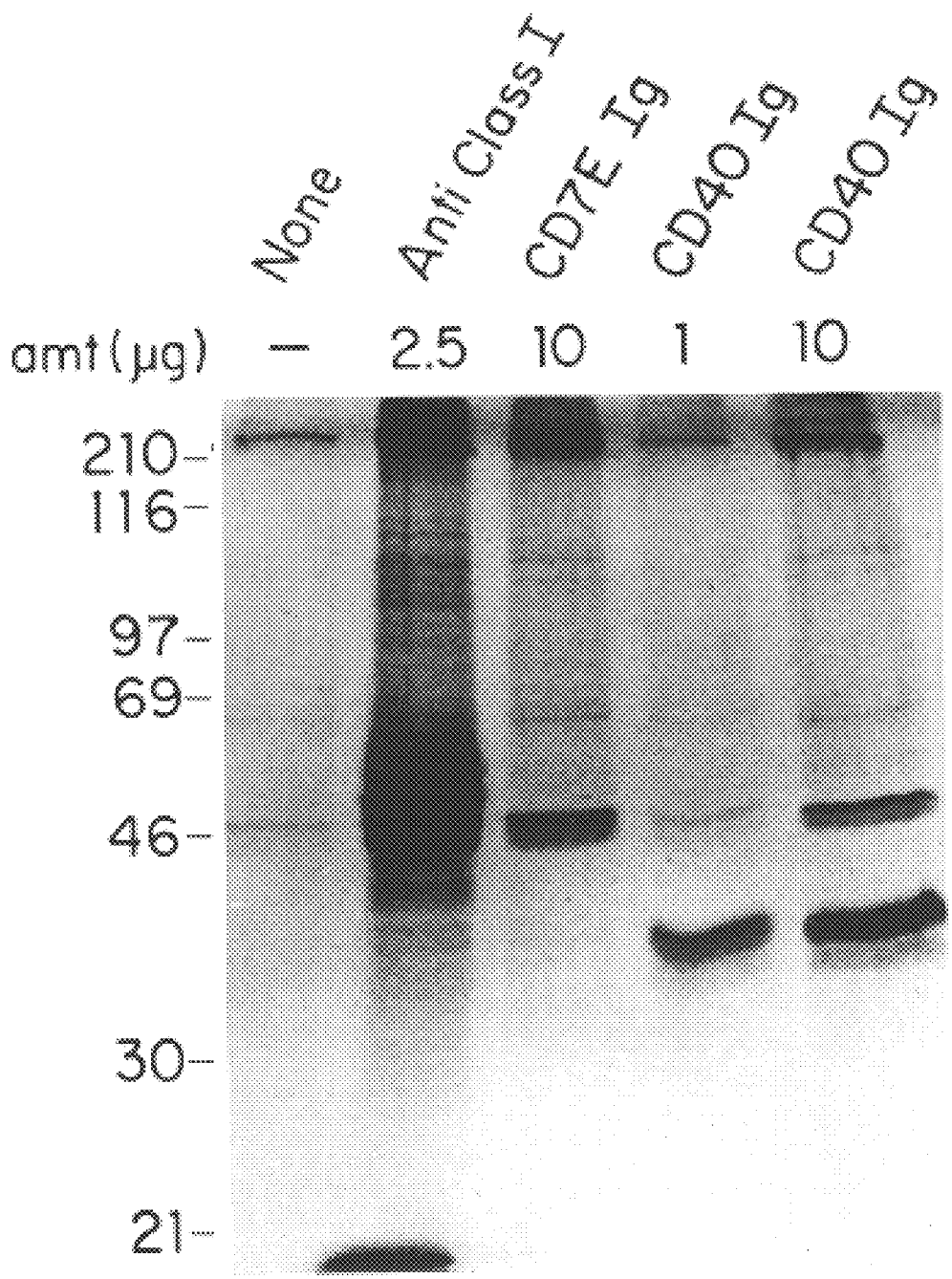

FIG. 4. CD40-Ig immunoprecipitated a 39 kD protein from lysate of activated T$_h$1. T$_h$1 were rested or activated with insolubilized anti-CD3 for 16 hours. [$^{35}$S]-labelled proteins from resting or activated T$_h$ were immunoprecipitated with purified antibodies or fusion proteins (1–10 μl). The gel profile is representative of 3 such experiments.

Figure 5:
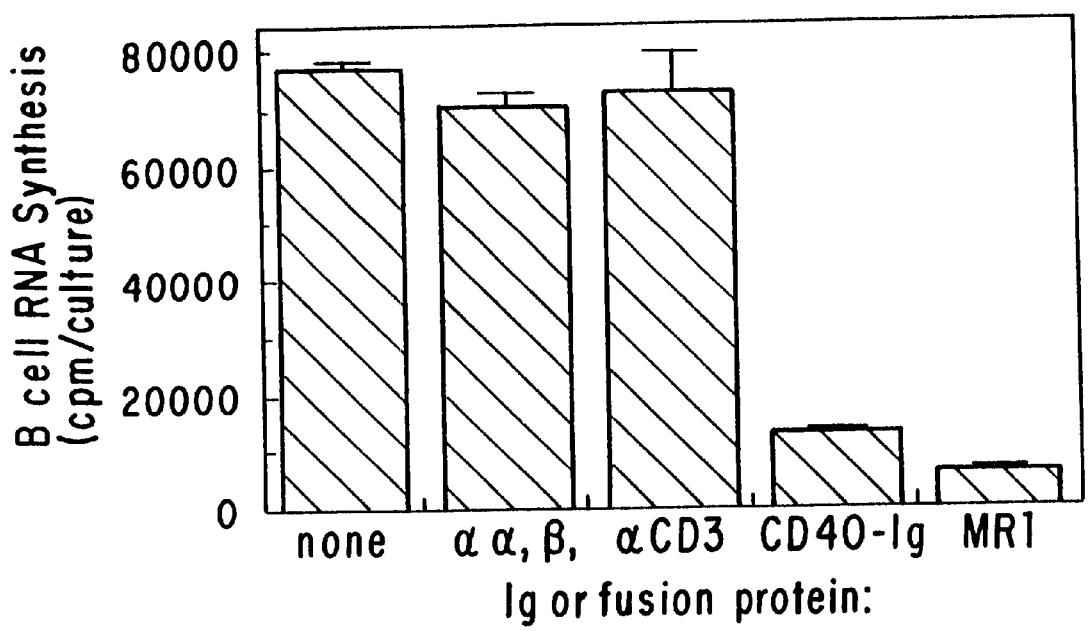

FIG. 5. A monoclonal antibody (mab), specific to the induced 39 Kd T$_h$ membrane protein, inhibited induction of B-cell RNA synthesis by PM$^{Act}$. Resting B-cells and PM$^{Act}$ were cultured with 10 μg/ml each of anti-α/β, anti-CD3, CD40-Ig or MR1. RNA synthesis was determined as described in FIGS. 1A–C. Results presented are the arithmetic means of triplicate cultures+/−s.d., and are representative of 3 such experiments.

Figures 6A, 6B:
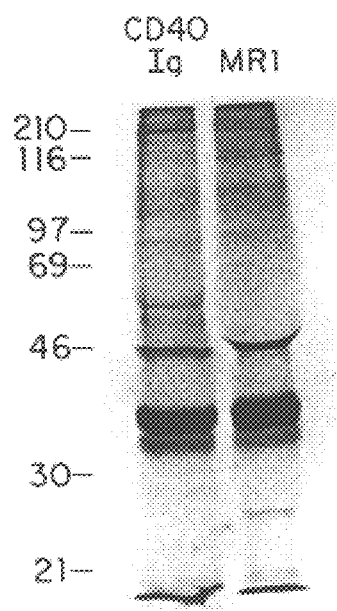

FIGS. 6A–6B. MR1 and CD40-Ig recognized the same molecule expressed on activated T$_h$.

FIG. 6A: Activated T$_h$ were fluorescently stained with MR1 or control Ig. To evaluate if CD40-Ig and MR1 competed for binding to activated T$_h$, graded concentrations of MR1 or control hamster Ig (anti-α/βTCR) were added together with anti-CD40 (20 μng/ml). After incubation for 20 minutes at 4° C., the samples were washed and incubated with FITC-conjugated, mab anti-human IgG$_1$. Results are representative of 3 such experiments.

FIG. 6B: Proteins from [$^{35}$S]-methionine-labelled, activated T$_h$ were immunoprecipitated with MR1 (10 μg/sample) or CD40-Ig (10 μg/sample) and resolved by PAGE and fluorography. Results presented are representative of 2 such experiments.

Figure 7A:
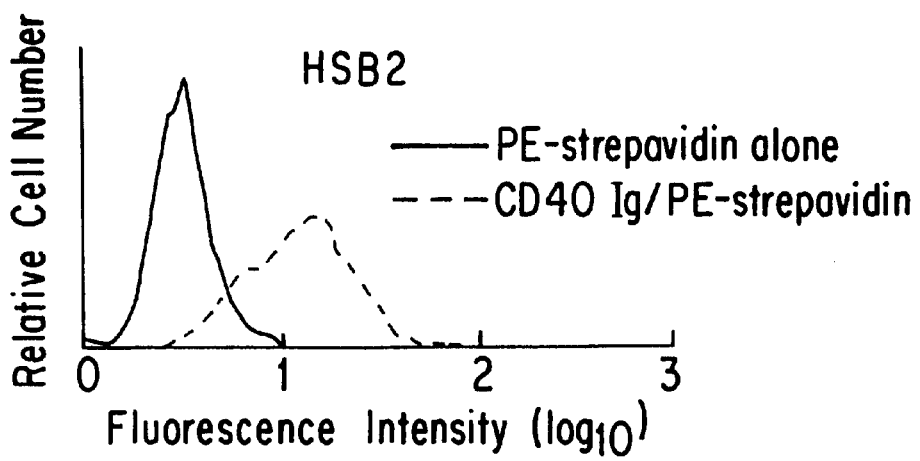
Figure 7B:
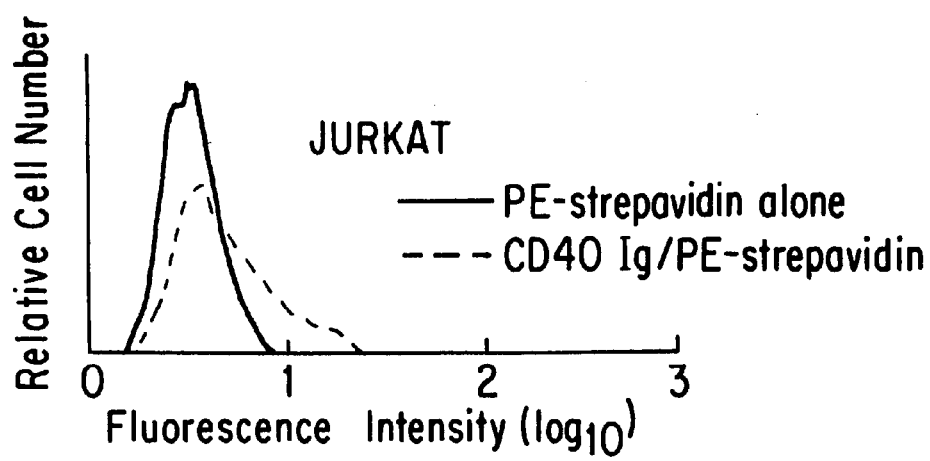
Figure 7C:
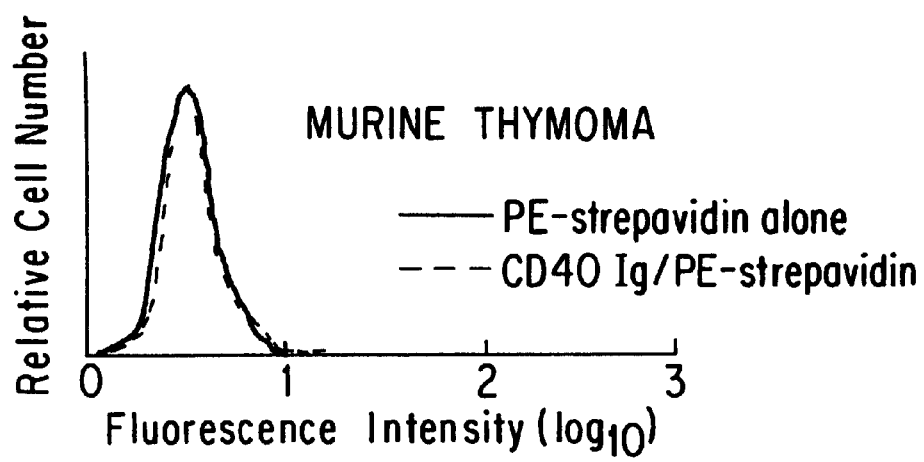

FIGS. 7A–7C. Binding of CD40-Ig to human cell lines. A variety of human T-cell lines were exposed to biotin-labelled CD40-Ig, and binding was evaluated by flow cytometry.

FIG. 8

Panel A: Nucleotide sequence of CD40 cDNA from Stamenkovic et al., (1989) EMBO J. 8:1403–1410. The transmembrane region is underscored.

Panel B: Schematic diagram of a plasmid that may be used to express CD40-Ig. The amino acid sequence at the site of fusion of Δ CD40 is shown below the diagrammed portion of CD40 (SEQ ID NO:3).

5. DETAILED DESCRIPTION OF THE INVENTION

The present invention provides for a substantially purified CD40CR receptor; for soluble ligands of CD40CR, including antibodies as well as fusion molecules comprising CD40; and for methods of controlling B-cell activation.

For purposes of clarity of disclosure, and not by way of limitation, the detailed description of the invention is divided into the following subsections:

| (i) | ligands that bind to CD40CR; |
|---|---|
| (ii) | methods used to characterize CD40CR; |
| (iii) | preparation of purified CD40CR; |
| (iv) | uses of ligands that bind to CD40CR; and |
| (v) | uses of CD40CR. |

5.1. Ligands that Bind To CD40CR

The present invention provides for soluble ligands of CD40CR, including (i) fusion molecules comprising at least a portion of CD40 protein and (ii) antibodies or antibody fragments.

The term "soluble," as used herein, indicates that the ligands of the invention are not permanently associated with a cell plasma membrane. Soluble ligands of the invention may, however, be affixed to a non-cellular solid support, including a lipid, protein, or carbohydrate molecule, a bead, a vesicle, a magnetic particle, a fiber, etc. or may be enclosed within an implant or vesicle.

The ability of such a ligand to bind to CD40CR may be confirmed by demonstrating that the ligand binds to the same protein as CD40-Ig (infra) or MR1 (infra).

The ligands of the invention may be comprised in pharmaceutical compositions together with a suitable carrier.

5.1.1. Fusion Molecules

The present invention provides for soluble fusion molecules that are ligands of CD40CR. Such fusion molecules comprise at least a portion of CD40 protein attached to a second molecule. The portion of CD40 preferably lacks the CD40 transmembrane domain. A portion of CD40 protein which may be used according to the invention is defined as any portion which is able to bind to CD40CR, for example, such a portion may be shown to bind to the same protein as MR1 or CD40-Ig.

Second molecules which may be used include peptides and proteins, lipids, and carbohydrates, and, in preferred embodiments of the invention, may be an immunoglobulin molecule, or portion thereof (such as an Fv, Fab, F(ab')$_2$, or Fab' fragment) or CD8, or another adhesion molecule, such as B7. The second molecule may be derived from either a non-human or a human source, or may be chimeric. The second molecule may also be an enzyme, toxin, growth factor, lymphokine, antiproliferative agent, alkylating agent, antimetabolite, antibiotic, vinca alkaloid, platinum coordinated complex, radioisotope, or a fluorescent compound.

The fusion molecules of the invention may be produced by chemical synthesis or, preferably, by recombinant DNA techniques.

For example, a nucleic acid sequence encoding at least a portion of CD40 protein may be combined with a nucleic acid sequence encoding a second molecule in a suitable expression vector, and then expressed in a prokaryotic or, preferably, eukaryotic expression system, such as a yeast, baculovirus, or mammalian expression system, including transgenic animals.

Alternatively, at least a portion of CD40 protein may be expressed using recombinant DNA techniques and then may be chemically conjugated to a second molecule.

Fusion molecules comprising CD40 may be purified from preparative mixtures using electrophoretic techniques or affinity chromatography using ligand that binds to either CD40 or to the second molecule. Ligands that bind to CD40 include, but are not limited to, anti-CD40 antibodies such as G28-5, as produced by the hybridoma having accession number HB9110 and deposited with the American Type Culture Collection, and CD40CR, described more fully in sections 5.2 and 5.3, infra. If the second molecule is an immunoqlobulin or immunoglobulin fragment, an affinity column comprising anti-immunoglobulin antibody may be used; if the second molecule comprises an F$_c$ fragment, a protein A column may be used.

According to a preferred embodiment of the invention, a portion of CD40 may be produced using a nucleic acid sequence that encodes a CD40 protein that is truncated upstream from the transmembrane domain. Such a nucleic acid sequence may be prepared by digesting a plasmid containing a cDNA encoding CD40 antigen, such as that described in Stamenkovic et al., (1989), *EMBO J.* 8:1403–1410, with PstI (P) and Sau 3A (S3) restriction enzymes. The resulting P/S3 fragment may be subcloned into the same plasmid digested with P and Bam HI (B), to produce a truncated CD40 gene (see FIG. 8B).

Figure 8B:
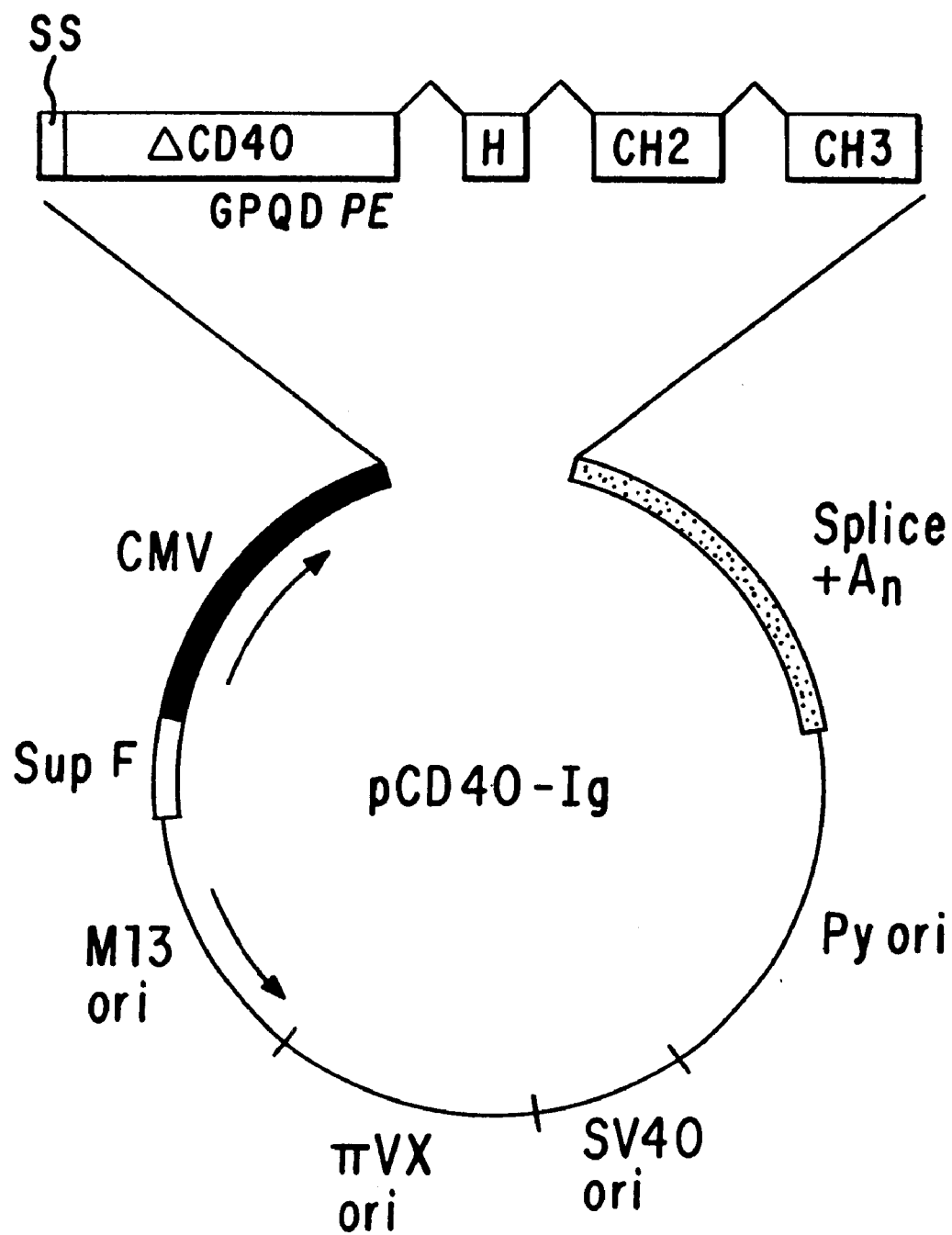

In particular, nonlimiting, embodiments of the invention, an expression vector used to produce ligands containing at least a portion of CD40 as well as immunoglobulin sequence may preferably comprise a virally-derived origin of replication, a bacterial origin of replication, a bacterial selectable marker, and eukaryotic promoter and enhancer sequences separated from DNA sequences encoding an immunoglobulin constant region by restriction endonuclease sites which allow subcloning of DNA sequences encoding at least a portion of CD40, followed by a polyadenylation signal sequence (see FIG. 8B).

In a specific embodiment of the invention, the truncated CD40 gene may be subcloned into an immunoglobulin fusion plasmid, such as that described in Aruffo et al., 1990, *Cell* 61:1303–1313, using an Mlu I and B digest, to form plasmid pCD40-Ig, which encodes the fusion molecule CD40-Ig (see FIG. 8B) CD40-Ig fusion protein may then be produced by transfecting the pCD40-Ig plasmid into COS cells to form a transient expression system. CD40-Ig produced may be collected from the COS cell supernatant and purified by protein A column chromatography as described in Aruffo et al., 1990, *Cell* 161:1303–1313.

5.1.2. Antibodies

The soluble ligands of the invention may comprise antibody molecules, monoclonal antibody molecules, or fragments of these antibody molecules which contain an antigen combining site that binds to CD40CR. Such ligands may further comprise a second molecule which may be a protein, lipid, carbohydrate, enzyme, toxin, growth factor, lymphokine, antiproliferative agent, alkylating agent, antimetabolite, antibiotic, vinca alkaloid, platinum coordinated complex, radioisotope, or a fluorescent compound and may be linked to the antibody molecule or fragment.

Where the ligand is a monoclonal antibody, or a fragment thereof, the monoclonal antibody can be prepared against CD40CR using any technique which provides for the production of antibody molecules by continuous cell lines in culture. For example, the hybridoma technique originally developed by Kohler and Milstein (1975, Nature 256:495–497) as well as other techniques which have more recently become available, such as the human B-cell hybridoma technique (Kozbar et al., 1983, Immunology Today 4:72) and EBV-hybridoma technique to produce human monoclonal antibodies (Cole et al., 1985, Monoclonal Antibodies and Cancer Therapy, Alan R. Liss, Inc., pp. 77–96) and the like are within the scope of the present invention.

Antibody fragments which contain the idiotype of the molecule could be generated by known techniques. For example, such fragments include but are not limited to: the F(ab')$_2$ fragment which can be generated by treating the antibody molecule with pepsin; the Fab' fragments which can be generated by reducing the disulfide bridges of the F(ab')$_2$ fragment; the F(ab')$_2$ fragment which can be generated by treating the antibody molecule with papain; and the 2Fab or Fab fragments which can be generated by treating the antibody molecule with papain and a reducing agent to reduce the disulfide bridges.

The present invention also provides for chimeric antibodies produced by techniques known in the art, such as those set forth in Morrison et al., (1984) *Proc. Natl. Acad. Sci. U.S.A.* 81:6851–6855 or European Patent Application No. 85305604.2, publication No. 0173494 by Morrison et al., published Mar. 5, 1986.

Immunogen for the production of antibodies may be any source that contains CD40CR. For example, activated T$_h$ may be used as an immunogen. Alternatively, substantially purified CD40CR, prepared as set forth in section 5.3, infra, may be used. If activated T$_h$ are used as immunogen, antiserum may be tested for reactivity against activated but not resting T$_h$ cells.

In a preferred embodiment of the invention, the soluble ligand is the MR1 monoclonal antibody. The following method was used to produce the MR1 monoclonal antibody, and may be used to generate other antibodies directed toward CD40CR.

Hamsters were immunized. intraperitoneally with 5–10$^6$ activated T$_h$1 cells (D1.6) at weekly intervals for six weeks.

When the serum titer against murine $T_h1$ was greater than about 1:10,000, cell fusions were performed with polyethylene glycol using immune hamster splenocytes and NSI. SN from wells containing growing hybridomas were screened by flow cytometry on resting and activated $T_h1$. One particular hybridoma, which produced a mab that selectively recognized activated $T_h$, was further tested and subcloned to derive MR1. MR1 was produced in ascites and purified by ion exchange HPLC.

The present invention also provides for ligands comprising monoclonal antibodies, and fragments thereof that are capable of competitively inhibiting the binding of MR1 to its target antigen or CD40-Ig to its receptor.

5.2. Methods used to Characterize CD40CR

CD40CR may be characterized by (i) its ability to bind CD40, fusion molecules comprising at least a portion of CD40, and antibodies such as MR1; (ii) its functional characteristic of being able to stimulate B-cell cycle entry, proliferation, and differentiation; and (iii) its cellular distribution.

5.2.1. Ability to Bind Ligands

CD40CR may be characterized by its ability to bind to ligands such as CD40, fusion molecules comprising CD40, and antibodies directed toward CD40CR.

As discussed in greater detail infra, several techniques were used to characterize CD40CR. For example, CD40-Ig and MR1 were shown to recognize the same 39 kD molecule. Both CD40-Ig and MR1 were found to immunoprecipitate a 39 kD protein from radiolabelled $T_h$ lysates (FIG. 6B). Further, immunoprecipitation of the 39 kD protein with CD40-Ig removed the antigen recognized by MR1 from $T_h$ lysates.

5.2.2. Ability to Stimulate B-cells

CD40CR may also be characterized by its ability to stimulate B-cell cycle entry, proliferation, and differentiation.

For example, plasma membrane (PM) from activated ($PM^{Act}$) but not resting ($PM^{rest}$) $T_h$ cells was found to induce B-cell RNA synthesis (FIG. 1a); this induction, indicative of B-cell activation, was not affected by antibodies such as anti-LFA-1, anti-CD4, anti-ICAM-1. CD40-Ig or MR1, however, were found to be able to inhibit $PM^{Act}$-induced B-cell activation, as shown in FIG. 1B and FIG. 5.

The induction of B-cell activation may be measured by techniques such as [$^3$H]-uridine incorporation into RNA (as B-cells differentiate, RNA synthesis increases), or by [$^3$H]-thymidine incorporation, which measures DNA synthesis associated with cell proliferation. For optimal measurement of the effect of CD40CR on B-cell proliferation, interleukin-4 (IL-4) may be added to the culture medium at a concentration of about 10 ng/ml.

Alternatively, B-cell activation may be measured as a function of immunoglobulin secretion. For example, CD40CR, in substantially purified form, or as present in PM, or otherwise, may be added to resting B-cells together with IL-4 (10 ng/ml) and IL-5 (5 ng/ml). After three days of culture, an additional volume of culture medium may be added. On day 6 of culture, supernatant (SN) from individual cultures may be harvested and quantitated for IgM and IG, as described in Noelle et al., (1991) *J. Immunol.* 146:1118–1124.

5.2.3. Cellular Distribution

CD40CR may also be characterized by its cellular distribution. For example, CD40-Ig was observed to bind to activated, but not resting $T_h1$, as assessed by flow cytometry (FIGS. 3A–3B). Furthermore, CD40-Ig was observed to bind to Jurkat cells, HSB2 cells, and activated T-cells from human peripheral blood, but did not appear to bind significantly to CEM cells, HPBALL cells, or murine thymoma cells.

For example, and not by way of limitation, the presence of CD40CR on a particular cell type ("test cells") may be evaluated by flow cytometry as follows. Test cells may be tested in parallel with resting (negative control) and activated (positive control) $T_h$ cells. All cells may be incubated at a concentration of about $1 \times 10^5$ cells/50 µl with ligand (e.g. CD40-Ig or MR1) for 20 minutes at 4° C., followed by FITC-conjugated anti-ligand antibody. Propidium iodide may be added to all samples to a final concentration of 2 µg/ml. Flow cytometric analysis may then be performed, for example on a BD FACSCAN. After positive gating of cells by forward versus side scatter, and by red negativity (for propidium iodide exclusion), and the log green fluorescence of viable cells may be ascertained.

5.3. Preparation of Purified CD40CR

The present invention provides for substantially purified CD40CR. Such CD40CR may be prepared from cells bearing CD40CR, such as activated helper T-cells, Jurkat, and HSB2 cells, by the following method.

Plasma membranes may be prepared from appropriate cells, such as activated $T_h1$ cells, by discontinuous sucrose gradient sedimentation, as described in Noelle et al., 1991, *J. Immunol.* 146:1118–1124. CD40CR may then be isolated by dissociating the crude membrane extract with mild detergent, and then performing size exclusion chromatography followed by either affinity chromatography using appropriate ligands (e.g. MR1 or CD40-Ig) bound to a solid support, immunoprecipitation (e.g. by CD40-Ig or MR1), and/or gel electrophoresis.

The resulting protein may be expected to have a molecular weight of about 39 kD.

The present invention provides for a soluble CD40CR (i.e. cell-free) which may be comprised in pharmaceutical compositions together with a suitable carrier. It further provides for CD40CR which is linked to a second molecule which may be a peptide, protein, lipid, carbohydrate, enzyme, toxin, growth factor, lymphokine, antiproliferative agent, alkylating agent, antimetabolite, antibiotic, vinca alkaloid, platinum coordinated complex, radioisotope, or a fluorescent compound.

The present invention further provides for substantially purified CD40CR which has been prepared by chemical synthesis or recombinant DNA techniques. For example, the gene for CD40CR may be isolated by inserting cDNA prepared from activated helper T-cells into the λgt10 expression system, and then screening with MR1 or CD40-Ig binding to identify CD40CR-expressing clones. Alternatively, cDNA prepared from activated helper T-cells may be transfected into COS cells, the supernatants of which may be screened with MR1 or CD40-Ig to identify CD40CR producers. The gene for CD40CR may be then used to express CD40CR using expression systems known in the art.

5.4. Uses of Ligands that Bind to CD40CR

The present invention provides for methods of controlling B-cell activation that utilize ligands that bind to CD40CR. In particular, it provides for a method of inhibiting B-cell activation comprising exposing a mixture of B-cells and $T_h$ cells to an effective concentration of ligand that binds to CD40CR. Ligands that may be used are described supra in section 5.1. The method of the invention may be practiced in vitro or in vivo. An effective concentration refers to a concentration of a ligand that inhibits B-cell activation, measured by any technique known in the art (including those set forth in section 5.2, supra) by at least about 30 percent, and preferably by about 75 percent. According to a preferred, specific, non-limiting embodiment of the invention, CD40-Ig may be used as ligand, in which case an effective concentration may be at least about 10 µg/ml. In another specific, nonlimiting embodiment of the invention, the monoclonal antibody MR1 may be used, in which case an effective concentration may be at least about 10 µg/ml. If the method is practiced in vivo, an effective concentration of ligand may refer to plasma concentration of ligand or to a local concentration. For example, it may be desirable to inhibit B-cell activation in a localized area in order to limit the effects on the immune system as a whole.

In particular embodiments, the invention provides for a method of treating a subject suffering from a disorder associated with B-cell activation, comprising administering to the subject a therapeutic amount of ligand that binds to CD40CR. A subject may be a non-human or, preferably, a human animal.

Disorders associated with B-cell activation include, but are not limited to, allergy (including anaphylaxis); autoimmune conditions including drug induced lupus, systemic lupus erythematosus, adult rheumatoid arthritis, juvenile rheumatoid arthritis, scleroderma, Sjogren's Syndrome, etc.; and viral diseases that involve B-cells, including Epstein-Barr infection, and retroviral infection including infection with a human immunodeficiency virus.

Because it has been suggested that B-cell activation is associated with the induction of human immunodeficiency virus replication from latency, it may be desirable to administer the ligands of the invention to HIV positive individuals who have not yet developed AIDS or ARC.

Ligands may be administered, in a suitable pharmaceutical carrier, by any method known in the art, including intravenous, intraperitoneal, subcutaneous, intrathecal, intraarticular or intramuscular injection, and oral, intranasal, intraocular and rectal administration, and may be comprised in microspheres, liposomes, and/or sustained release implants.

A therapeutic amount of ligand is defined as an amount which significantly diminishes the deleterious clinical effects of B-cell activation, and may vary among ligands used and conditions treated. If CD40-Ig is used, therapeutic concentration may be about 10 µg/ml either. systemically (plasma concentration) or locally. If MR1 is used, a therapeutic concentration may be about 10 µg/ml either systemically (plasma concentration) orplocally.

In a further embodiment of the invention, the above methods may utilize a ligand comprising a toxin or antimetabolite such that $T_h$ cells are killed or damaged and B-cell activation is decreased as a result of $T_h$ cell destruction.

The ligands of the invention may also be used to label activated T cells, a technique which may be useful in the diagnosis of T cell disorders. To this end, ligand comprising an enzyme, cradioisotope, fluorescent compound or other detectable label may be exposed to T cells in vitro or in vivo and the amount of binding may be quantitated.

The ligands of the invention may also be used to deliver substances, e.g. growth factors, to activated T-cells.

5.5. Uses of CD40CR

The present invention provides for methods of controlling B-cell activation that utilize CD40CR or a molecule comprising CD40CR, prepared as described in section .5.3, sura. In particular, it provides for a method of promoting B-cell activation comprising exposing B-cells to an effective concentration of CD40CR. The method may be practiced in vivo or in vitro. An effective concentration refers to a concentration of receptor that induces B-cell activation, measured by any technique known in the art (including those set forth in section 5.3, supra) by at least about 30 percent. In specific, nonlimiting embodiments of the invention, the concentration of CD40CR may be about 10 µg/ml locally or systemically.

In particular embodiments, the invention provides for a method of treating a subject suffering from an immunodeficiency disorder associated with diminished humoral immunity, comprising administering to the subject a therapeutic amount of CD40CR. A subject may be a non-human or, preferably, a human animal.

Immunodeficiency disorders associated with diminished humoral immunity include acquired immunodeficiency syndrome, immunodeficiency associated with malignancy or cachexia, iatrogenic immunodeficiency caused, for example, by chemotherapy or radiation therapy, as well as genetic disorders involving humoral immunity.

CD40CR may be administered,in a suitable pharmaceutical carrier, by any method known in the art, including intravenous, intraperitoneal, subcutaneous, intrathecal, intraarticular, or intramuscular injection, and oral,intranasal, intraocular, and rectal administration and may be comprised in microspheres, liposomes, and/or sustained release implants.

A therapeutic amount of CD40CR for CD40 is defined as that amount which increases immunoglobulin production by at least about 30 percent.

In a further embodiment, CD40CR may be conjugated to a toxin, and then administered to a subject under circumstances in which it would be preferable to destroy B-cells that express CD40. Examples of such circumstances include patients receiving organ transplants or suffering from multiple myeloma or another B-cell malignancy,or from autoimmune disease.

CD40CR may also be used to label B-cells expressing CD40, a technique which may be useful in the diagnosis of B-cell disorders. To this end, receptor linked to an enzyme, radioisotope, fluorescent compound or other detectable label may be exposed to B-cells in vivo or in vitro and the amount of binding may be quantitated.

CD40CR may also be used to deliver molecules that are linked to it to B-cells.

6. EXAMPLE; A NOVEL RECEPTOR, CD40CR, ON ACTIVATED HELPER T-CELLS BINDS CD40 AND TRANSDUCES THE SIGNAL FOR COGNATE ACTIVATION OF B-CELLS

6.1. Materials and Methods 6.1.1. Animals

Female DBA/2J mice (Jackson Laboratories, Bar Harbor, Me.) were used for the preparation of filler cells to support the growth of $T_h$ clones and in the preparation of resting B-cells.

6.1.2. Helper T-cell Clones ($T_h$)

D1.6, a I-A$^d$-restricted, rabbit Ig-specific $T_h1$ clone (Kurt-Jones et al., (1987) *J Exp Med* 166:1774–1787) was obtained from Dr. David Parker, University of Mass. at Worcester. D1.6 will be referred to herein as $T_h1$.

6.1.3. Activation of $T_h$ by Anti-CD3

$T_h1$ were cultured ($8\times10^6$/well) in cluster wells (6 well, Corning, N.Y.) coated with 40 μg/4 ml of PBS/well with anti-CD3 for 16 hours, as described in (Noelle et al., (1991) *J. Immunol.* 146:1118–1124).

6.1.4. Preparation of $T_h$ Plasma Membranes

Plasma membranes were prepared by discontinuous sucrose gradient sedimentation, as described in (Noelle et al., (1991) *J. Immunol.* 146:1118–1124).

6.1.5. Preparation of Resting B-cells

Resting splenic B-cells were prepared by sedimentation on discontinuous Percoll gradients, as described in (Defranco et al., (1982) *J. Exp. Med.* 155:1523). Cells isolated from the 70–75% (density of 1.087–1.097) Percoll interface were typically >95% mIg⁺, had a uniform, low degree of near forward light scatter and were unresponsive to Con A.

6.1.6. Antibodies

The following mabs were purified by ion exchange HPLC from ascites fluid of mice which had been irradiated and bone marrow reconstituted: anti-CD3:145–2C11 (Leo et al., (1987) *Proc. Natl. Acad. Sci. USA* 84:1374–1378); anti-α, β:H57–597; anti-CD4: GK1.5 (Wilde et al., (1983) *J. Immunol.* 131:2178–2183); anti-ICAM:YN1/1.7.4 (Prieto et al., (1989) *Eur. J. Immunol.* 19:1551–1557); anti-LFA-1: FD441.8 (Sarmiento et al, (1982) *Immunol. Rev.* 68:135); and anti-rat/hamster κ chain:RG-7 (Springer, (1982) *Hybrid.* 1:257–273).

6.1.7. Preparation of the CD40 Recombinant Globulin (CD40-Ig)

The CD40 fusion protein was prepared by digesting a plasmid containing a cDNA encoding the CD40 antigen (Stamenkovic and Seed, (1989) *EMBO J.* 8:1403–1410) with the restriction enzyme Pst I (P) and Sau 3A (S3). This P/S3 fragment was subcloned into the same plasmid digested with P and Bam H1 (B). This allowed the preparation of the CD40Δ which encoded a CD40 protein truncated upstream from the transmembrane domain. The DNA fragment encoding a CD40Δ was then subcloned into the immunoglobulin fusion plasmid (Aruffo et al. (1990), *Cell.* 61:1303–1313) using a MluI and B digest. The CD40-Ig fusion protein was produced by transient transfection in COS cells and purified on a protein A column as described in ((Aruffo et al., (1990) *Cell.* 61:1303–1313).

6.1.8. Lymphokines

Interleukin 4 (IL4): Recombinant mouse IL4 was generously provided by Drs. C. Maliszewski and K. Grabstein, Immunex Corporation, Seattle, Wash.

Interleukin 5 (IL5): Recombinant mouse IL5 was purchased from R&D Research, Sarrento, Calif.

6.1.9. Induction of B-cell RNA Synthesis by Activated $T_h$ Plasma Membranes $3\times10^4$ resting B-cells were cultured in 50 μl of cRPMI in A/2 microtiter wells (Costar, Cambridge, Mass.). To these wells, 0.5 μg of $T_h1$ or $T_h2$ membrane protein was added. From 42–48 hrs, wells were pulsed with 2.5 μCi of ³H-uridine (New England Nuclear, Boston Mass.), harvested, and the radioactivity determined by liquid scintillation spectroscopy. The results were expressed as cpm/culture+/–s.d.

6.1.10. Induction of B-cell Immunoglobulin Secretion by Activated $T_h$ Plasma Membranes and Lymphokines Resting B-cells were cultured as described above. To culture wells, 0.5 μg of $T_h1$ membrane protein, IL4 (10 ng/ml) and IL5 (5 ng/ml) were added. On day three of culture, an additional 50 μl of cRPMI was added. On day six of culture, SN from individual wells were harvested and quantitated for IgM and $IgG_1$, as described in (Noelle et al., (1991) *J. Immunol.* 146:.1118–1124).

6.1.11. Induction of B-cell Proliferation by Activated $T_h$ and IL4

$4\times10^4$ resting B-cells were cultured in 50 μl of CRPMI in A/2 microtiter wells (Costar, Cambridge, Mass.). To these wells, $1\times10^4$ resting or activated, irradiated (500 rads) $T_h1$ and IL4 (10 ng/ml) were added. On day three of culture, wells were pulsed with 1 μCi of ³H thymidine, as described in (Noelle-etal., (1991) *J. Immunol.* 146:1118–1124).

6.1.12. Production of Monoclonal Antibodies Specific to Membrane Proteins Induced on Activated $T_h1$ Hamsters were immunized intraperitoneally with 5–10× $10^6$ activated $T_h1$ (D1.6) at weekly intervals for six weeks. When the serum titer against murine $T_h1$ was greater than 1:10,000, cell fusions were performed with polyethylene glycol using immune hamster splenocytes and NS1. SN from wells containing growing hybridomas were screened by flow cytometry on resting and activated $T_h1$. One particular hybridoma, which produced a mab that selectively recognized activated $T_h$, was further tested and subcloned to derive MR1. MR1 was produced in ascites and purified by ion exchange HPLC.

6.1.13. Flow Cytofluorometric Analysis of Activation Molecules Expressed on $T_h$ Resting and activated $T_h$ (16 hours with anti-CD3) were harvested and incubated at $1\times10^5$ cells/50 μl with fusion protein for 20 minutes at 4° C., followed by FITC-conjugated goat anti-human (h)IgG (25 μg/ml; Southern Biotechnology, Birmingham, Ala.). To all samples, propidium iodide was added at final concentration of 2 μg/ml. Flow cytofluorometric analysis was performed on a BD FACSCAN. After positive gating of cells by forward versus side scatter, and by red negativity (for propidium iodide exclusion), the log green fluorescence of viable cells was ascertained. At least 5,000 viablecells were analyzed for the determination of percent positive cells and MFI. Staining with MR1 employed FITC-conjugated RG7, a mouse anti-rat/hamster κ chain mab.

6.1.14. Biosynthetic Labelling, Immunoprecipitation, SDS-page and Fluorography $T_h1$ were rested or activated with insolubilized anti-CD3 for 16 hrs. Proteins from resting and activated $T_h$ ($20\times10^6$/ml) were labelled with 1 mCi of [³⁵S]-methionine/cysteine for one hour, at which time they were washed twice in RPMI/10%FCS and the cell pellet was lysed in extraction buffer,as described (Noelle et al., (1986) *J. Immunol.* 137:1718–1726). Purified antibodies or fusion proteins (1–10 μg) were added to 500 μl of lysate ($5\times10^6$ cell equivalents) at 4° C. for 16 hours. At that time, the lysates were transferred to tubes containing 50 μl of packed Protein A-sepharose. The pelleted Protein A-Sepharose was resuspended and tubes were incubated at 4° C. for 1 hr with agitation. The samples were then washed 3× with high stringency wash buffer. The pelleted protein A-Sepharose was resuspended in 30 μl of SDS sample buffer and run on a 10% polyacrylamide gel. After running the gel, the gel was fixed and fluorography performed.

6.2. Results

6.2.1. Effect of Monoclonal Antibodies on the Induction of B-cell RNA Synthesis by $PM^{Act}$ In order to define the cell surface molecules that mediated the induction of B-cell cycle entry by $PM^{Act}$, mabs to $T_h$ membrane proteins were added to cultures of $PM^{Act}$ and B-cells. $PM^{Act}$ induced B-cell RNA synthesis eight-fold over that observed with $PM^{rest}$) (FIG. 1*a*). The addition of anti-LFA-1, anti-CD4, anti-ICAM-1, alone, or in combination, did not inhibit the induction of B-cell RNA synthesis by $PM^{Act}$.

6.2.2. CD40-Ig Inhibited $T_h$-Induced B-cell Cycle Entry, Differentiation and Proliferation In the human system, it had been shown that anti-CD40 mab induced B-cell proliferation (Clark and Lane, (1991) Ann. Rev. *Immunol.* 9:97–127) thereby implicating CD40 as an important triggering molecule for B-cells. To determine if CD40 was involved in the induction of B-cell RNA synthesis by $PM^{Act}$, a soluble fusion protein of the extracellular domains of human CD40 and the $F_c$ domain of human $IgG_1$ (CD40-Ig) was added to cultures of $PM^{Act}$ and B-cells. $PM^{Act}$ derived from $T_h1$ and $T_h2$ were prepared and used to stimulate B-cell RNA synthesis. The addition of CD40-Ig to culture caused a dose-dependent inhibition of B-cell RNA synthesis that was induced by $PM^{Act}$ from $T_h1$ and $T_h2$ (FIG. 1b). Half-maximal inhibition of B-cell RNA synthesis induced by $PM^{Act}$ from $T_h1$ and $T_h2$ was about 5 μg/ml CD40-Ig. A CD7E-Ig fusion protein (Damle and Aruffo, (1991) *Proc. Natl. Acad. Sci. USA* 88:6403–6407) was without effect even when used at 25 μg/ml.

To investigate whether CD40-Ig inhibited the activation of B-cells by T-independent activators, B-cells were cultured in the presence of LPS and CD40-Ig. On day 2, RNA synthesis was assessed (FIG. 1c). CD40-Ig was ineffective at inhibiting B-cell activation by LPS, yet inhibited the response of B-cells to $PM^{Act}$.

In the presence of $PM^{Act}$, IL4 and IL5, B-cells polyclonally differentiated to produce Ig (Hodgkin et al., (1990) *J. Immunol.* 145:2025–2034; Noelle et al., (1991) *J. Immunol.* 146:1118–1124). To evaluate the requirements for CD40 signalling in this process, CD40-Ig was added at the initiation of culture, or on subsequent days of culture. The addition of CD40-Ig (FIG. 2a) at the initiation of culture inhibited greater than 95% of polyclonal IgM and $IgG_1$ production compared to control levels in its absence. In contrast, the addition of CD40-Ig on day 1 and 2 of culture showed little, if any, inhibitory effect on IgM and $IgG_1$ production. These data indicated that after 24 hours, signalling via CD40 is no longer essential for the differentiation of B-cells to Ig secretion.

Data thus far indicated that CD40 was implicated in the activation of B-cells by $PM^{Act}$. Studies were performed in order to ensure that CD40 was also involved in the activation of B-cells by intact, viable, activated $T_h$. $T_h1$ were activated for 16 hours with insolubilized anti-CD3, harvested and irradiated. The irradiated $T_h1$ were cultured with B-cells in the presence of IL4 and B-cell proliferation was determined on day 3 of culture. An exogenous source of IL4 was required to achieve B-cell proliferation with $T_h1$, because $T_h1$ do not produce IL4 (Noelle et al., (1989) *J. Immunol.* 143:1807–1814). CD40-Ig inhibited the induction of B-cell proliferation by irradiated $T_h$ in a dose-dependent manner, similar to that observed with $PM^{Act}$ (FIG. 2b). The negative control, CD7E-Ig, exerted no appreciable effect.

6.2.3. CD40-Ig Detected a Molecule Expressed on Activated, but not Resting $T_h$ To investigate whether activated $T_h1$ express a binding protein for CD40, resting and activated (16 hours) $T_h1$ were stained with CD40-Ig or CD7E-Ig, followed by FITC-anti-HIgG. Binding of CD40-Ig was assessed by flow cytometry (FIGS. 3A–3B). $T_h1$ that were activated for 16 hours with anti-CD3, but not resting $T_h1$, stained 56% positive with CD40-Ig, but not with the control CD7E-Ig. To identify the CD40-Ig binding protein, $T_h1$ proteins were biosynthetically labelled with [$^{35}$S]-methionine/cysteine and proteins immunoprecipitated with CD40-Ig or CD7E-Ig. The immunoprecipitated proteins were resolved by SDS-PAGE and fluorography (FIG. 4). A prominent band with an apparent molecular weight of 39 kD immunoprecipitated in a dose-dependent manner with 1 and 10 μg of CD40/sample. As controls, anti-class I mab immunoprecipitated bands at 55 kD and a low molecular weight band, β2 microglobulin. In the absence of mab, no prominent bands were visible. A 39 kd band was also immunoprecipitated from activated $T_h$ that were vectorially labelled with $^{125}$I, confirming that the 39 kD protein was a membrane protein.

6.2.4. Monoclonal Antibody MR1, Specific to 39 Kd $T_h$ Membrane Protein, Inhibited the Induction of B-cell RNA Synthesis by $PM^{Act}$ Mabs specific to antigens selectively expressed on activated versus resting $T_h$ were developed to identify $T_h$ molecule(s) responsible for the $T_h$ effector phase activity. One such mab, MR1, recognized an antigen that was selectively expressed on activated $T_h1$. To investigate whether MR1 and CD40-Ig recognized the same molecule, flow cytometry and blocking studies were performed. CD40-Ig and MR1 stained approximately 56% and 61%, respectively, of activated, but not resting Th (FIG. 6A). MR1, but not another hamster anti-T cell mab, anti-α/β TCR, blocked the staining of activated $T_h1$ with CD40-Ig, in a dose-dependent manner. These data suggested that CD40-Ig and MR1 recognized overlapping or identical epitopes on the 39 kD Th protein. To further demonstrate that CD40-Ig and MR1 recognized the same molecule, the antigen that bound MR1 was identified by immunoprecipitation of proteins from radiolabelled Th lysates. Both CD40-Ig and MR1 immunoprecipitated a 39 kD protein (FIG. 6B). Finally, immunoprecipitation of the 39 kD protein with CD40-Ig removed the antigen recognized by MR1 from radiolabelled lysates of activated $T_h$ supporting the tenet that the MR1 antigen and the CD40 binding protein were identical.

Functional studies were performed with MR1 to address whether this mab neutralized the activity expressed by $PM^{Act}$. $PM^{Act}$ and B-cells were cultured alone, or in the presence of hamster mabs or CD40-Ig. Two hamster mabs, anti-α/β TCR and α-CD3 did not inhibit the activation of resting B-cells by $PM^{Act}$. In contrast, MR1 or CD40-Ig inhibited B-cell activation (FIG. 5).

6.3. Discussion

The data show that blocking of prominent $T_h$ surface molecules (LFA-1, CD4, ICAM-1, CD3, α,β TCR) with mabs did not impede the capacity of activated $T_h$ to induce B-cell cycle entry. In contrast, CD40-Ig or a maB specific to the CD40 binding protein; blocked $T_h$-dependent B-cell activation in a dose-dependent manner. Furthermore, the CD40 binding protein was identified as a 39 kD protein that is selectively expressed on the membranes of activated, but not resting $T_h$. Both CD40-Ig and a mab specific to the 39 kD CD40 binding protein blocked B-cell activation by $PM^{Act}$.

Although a number of membrane proteins have been implicated in $T_h$-dependent B-cell signalling, evidence presented herein dismisses the contribution of some molecules (LFA-1, CD4, CD3, α,β TCR, ICAM-1) and implicates CD40 as the B-cell receptor for cognate signalling by $T_h$. Data show that CD40-Ig and a mab specific to the CD40 binding protein inhibits $T_h$-dependent B-cell activation.

The ligand for CD40 is a 39 Kd protein that is expressed on activated, but not resting $T_h$. Biochemical studies indicate that the 39 kD protein is a single chain molecule since electrophoretic migration was not influenced by reducing agents. Based on the functional studies presented in this study, both activated $T_h1$ and $T_h2$ express the 39 kD CD40 binding protein. This is consistent with the functional studies that show both $T_h1$ and $T_h2$ induce B-cell cycle entry. In an attempt to further characterize the 39 kD protein, cDNA encoding CD proteins in the MW range of 39 kD (CD 53, CD27 and CD69) were transiently transfected into COS cells and the cells were tested for CD40-Ig binding. None of the transfected COS cells expressed proteins that bound CD40-Ig. It is therefore suspected that the 39 kD protein is not one of these CD proteins.

The biochemical basis for signal transduction between $T_h$ and B-cells has been elusive. The identification of CD40 as the signal transducing molecule for T cell help focusses attention on specific biochemical pathways known to be coupled to the CD40 molecule. CD40 is a member of the nerve growth factor receptor (NGFR) family by virtue of the presence of four cysteine-rich motifs in its extracellular region. Signaling through CD40 by mab has been shown (Uckun et al., (1991) *J. Biol. Chem.* 266:17478–17485) to involve the activation of tyrosine kinases resulting in the increased production of inositol trisphosphate and the activation of at least four distinct serine/threonine kinases. Based on information obtained from signaling through other members of the NGF receptor family, it is anticipated that interaction between activated $T_h$ and B will result in many of the same biochemical processes.

7. EXAMPLE

BINDING OF CD40 Ig TO HUMAN T-CELL LINES

For immunofluorescence binding studies, CD40 Ig fusion protein was conjugated with biotin using biotin-succinimide (Sigma). Flow cytometry analysis was then performed by tow-step staining using phycoerythrin (PE)-strepavidin (Bectin-Dickinson) with a Coulter Epics C instrument. Representative results of screening multiple T cell lines is presented below. The Jurkat and HSB2 cell lines were found to bind specifically, whereas other T cell lines including CEM, HPBALL, and murine thymoma did not bind the CD40 Ig fusion protein (FIGS. 7A–7C).

8. DEPOSIT OF HYBRIDOMA CELL LINE

Hybridoma MR1, which produces monoclonal antibody MR1, was deposited with the American Type Culture Collection, 12301 Parklawn Drive, Rockville, Md. 20852, on May 22, 1992 and was assigned accession number HB11048.

Various publications are cited herein which are hereby incorporated by reference in their entirety.

What is claimed is:

1. A substantially purified cell-free ligand which specifically binds to CD40CR, a 39 kD T-cell protein which binds to the CD40 B-cell antigen and stimulates B-cell cycle entry, proliferation, and differentiation, said ligand: (a) comprising at least a portion of the extracellular domain of a CD40 protein having a sequence as set forth in SEQ ID NO.: 1 attached to a second molecule, wherein said second molecule is selected from the group consisting of peptides, proteins, carbohydrates and lipids, and wherein the extracellular domain at the site of fusion has the amino acid sequence as set forth in SEQ ID NO.3, and said ligand (b) being capable of binding to said CD40CR protein on an activated helper T-cell and inhibiting the activation of a resting B-cell by the activated T-cell.

2. The ligand of claim 1 wherein the second molecule is at least a portion of an immunoglobulin molecule.

3. The ligand of claim 2 wherein the portion of an immunoglobulin molecule comprises a Fc fragment.

4. The ligand of claim 3 wherein the Fc fragment comprises a hinge, a CH2 and a CH3 region.

5. The ligand of claim 1 which is CD40-Ig, as produced by the plasmid pCD40-Ig depicted in FIG. 8B.

6. A substantially purified cell-free CD40/immunoglobulin fusion protein which specifically binds to mouse CD40CR, a 39 kD mouse T-cell protein which binds to the CD40 B-cell antigen and stimulates B-cell cycle entry, proliferation and differentiation, said fusion protein comprising at least a portion of the extracellular domain of a CD40 protein having a sequence as depicted in SEQ. ID. NO.:1, and wherein the extracellular domain at the site of fusion has the amino acid sequence as set forth in SEQ ID NO:3.

7. The fusion protein of claim 6 which specifically competitively inhibits the binding of CD40 to mouse CD40CR.

8. The fusion protein of claim 6 which specifically competitively inhibits the binding of a monoclonal antibody, as produced by hybridoma MR1, deposited with the American Type Culture Collection and assigned accession number HB11048, to its target antigen.

* * * * *